United States Patent [19]

Miljkovic et al.

[11] Patent Number: 5,723,589
[45] Date of Patent: Mar. 3, 1998

[54] CARBOHYDRATE CONJUGATED BIO-ACTIVE COMPOUNDS

[75] Inventors: Dusan Miljkovic, Costa Mesa; Zbigniew Pietrzkowski, Santa Ana; Esmir Gunic, Costa Mesa; Wilfried Seifert, La Jolla, all of Calif.

[73] Assignee: ICN Pharmaceuticals, Costa Mesa, Calif.

[21] Appl. No.: 576,817

[22] Filed: Dec. 21, 1995

[51] Int. Cl.$^6$ .................................................... C07H 1/00
[52] U.S. Cl. ................................................ 536/1.11; 536/124
[58] Field of Search ................................. 536/1.11, 124

[56] References Cited

U.S. PATENT DOCUMENTS

| 3,965,262 | 6/1976 | Gordon | 424/180 |
| 4,016,261 | 4/1977 | Gordon | 424/180 |

FOREIGN PATENT DOCUMENTS

WO 91/14969  3/1990  WIPO.

OTHER PUBLICATIONS

Akhtur, S., Routledge, A., Patel, R and Gardiner, J., Synthesis of Mono-and Dimannoside Phosphoramidite Derivatives for Solid–Phase Conjugation to Oligonucleotides, *Tetrahedron Letters*, 36:40, 7333–7336 (1995).

Molema, G., Jansen, R.W., Pauwells, R., Clerco, E., Meijer, D.K.F., Targeting of Antiviral Drugs to $T_4$-Lymphocytes, *Biochemical Pharmacology*, 40:12, 2603–2610 (1990).

*Primary Examiner*—John Kight
*Assistant Examiner*—Everett White
*Attorney, Agent, or Firm*—Crockett & Fish

[57] ABSTRACT

Methods and compositions are provided which increase the cellular uptake of bioactive materials by covalently bonding such compounds to carbohydrate moieties through chemical linkers using other than glycosidic bonds. Numerous carbohydrates, linkers and bioactive materials can be joined in this way to form novel compositions, which are collectively referred to herein as glinkosides. Preferred glinkosides are preferentially taken up by glucose receptor and/or other cellular receptors, and once inside the cells, the glinkosides are cleaved into a sugar, a linker or linker fragments, and a biologically active compound. Various aspects of the invention include processes for synthesizing glinkosides, glinkoside compositions, and methods of treating diseases using glinkosides.

15 Claims, 11 Drawing Sheets

SYNTHESIS OF DERIVATIZED LINKERS (ROUTE ADD' - OVERALL YIELD 71%)

Figure 2:
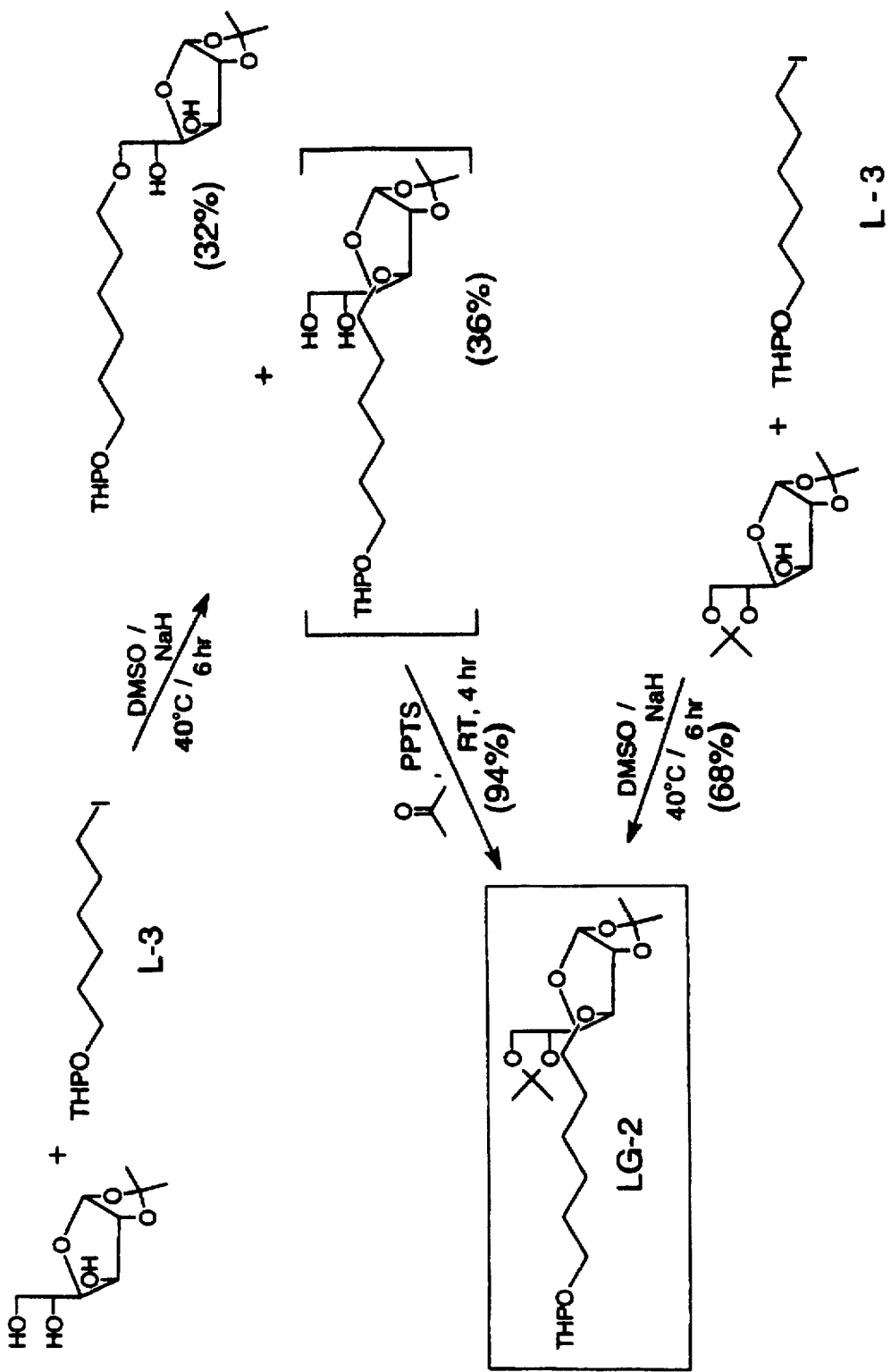

Fig. 2. SYNTHESIS OF 3-O- AND 6-O-D-GLUCOSE-LINKER INTERMEDIATES

Figure 7:
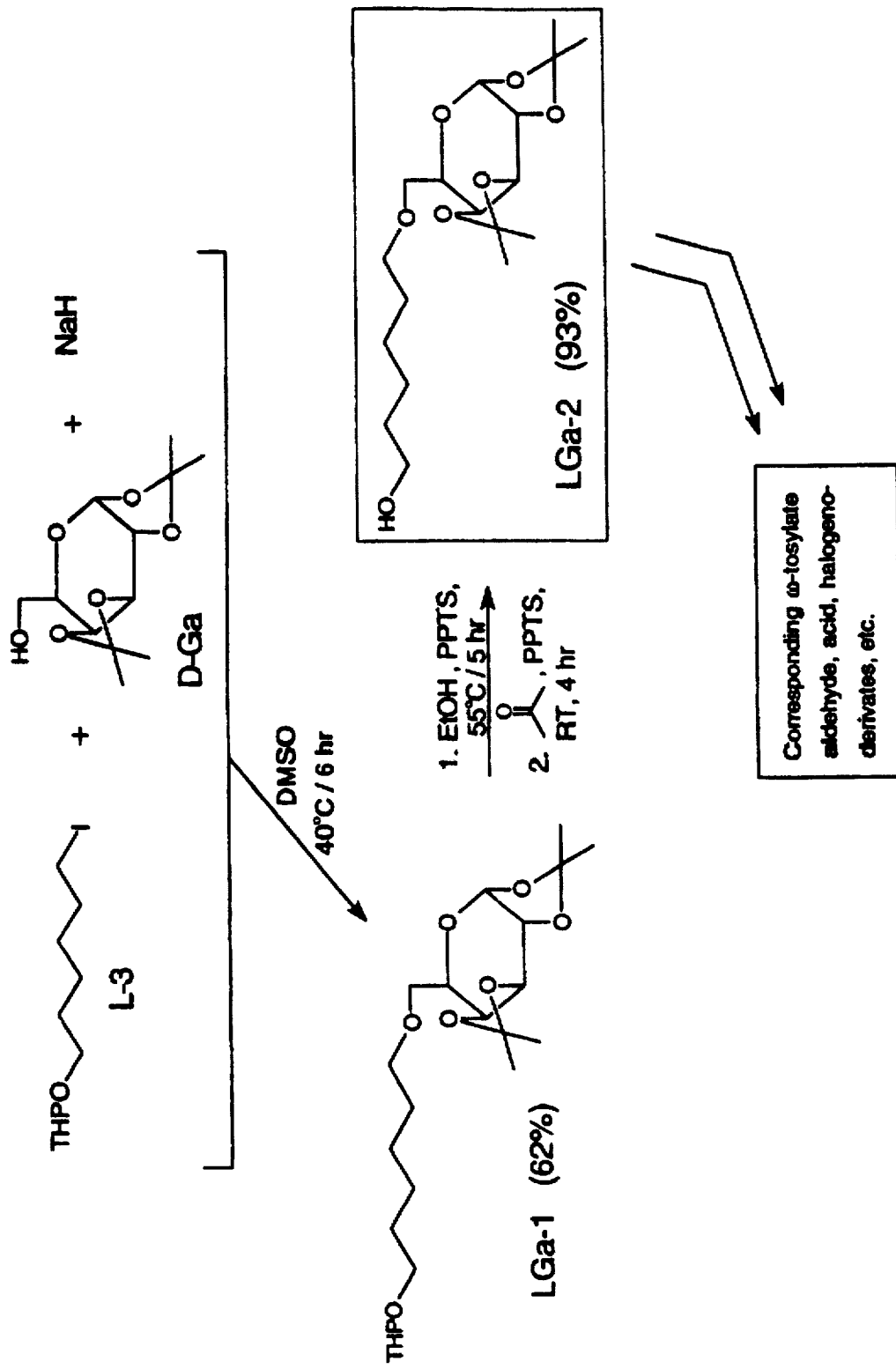

Fig. 7. SYNTHESIS OF 6-O-D-GALACTOSE-LINKER INTERMEDIATES

CARBOHYDRATE CONJUGATED BIO-ACTIVE COMPOUNDS

I. FIELD OF THE INVENTION

The field of the invention is delivery and targeting of bioactive materials, including especially the use of increased bioavailability and cellular uptake to affect such delivery and targeting.

II. BACKGROUND OF THE INVENTION

A significant problem in clinical pharmacology is the selective delivery of specific bio-active compounds to target cells of an organism. In many cases desirable compounds are only passively and partially diffused into target cells, and the plasma concentrations required to achieve significant intracellular levels are difficult to achieve due to toxicity, clearance and degradation by the liver, kidneys and other bodily organs or fluids. In conditions of the central nervous system the problem is often exacerbated by the blood brain barrier (BBB), and in neoplasms the problem may be further exacerbated due to poor or inefficient vascularization. Additional further difficulties may result from digestion or degradation of bio-active compounds within the gut, and/or poor transport of many such compounds across the intestinal wall. Still further difficulties arise from the inadvertent delivery of the bio-active compounds to non-targeted cells.

Problems related to specific delivery have been encountered with many bio-active compounds, including highly toxic anti-tumor drugs such as doxorubicin and methotrexate, antiviral drugs such as arabinosyl cytosine and arabinosyl adenosine, and antiparasitic drugs such as chloroquine and pyrimethamine in which cite specificity is particularly important. Delivery problems are also encountered with respect to substances which are not technically considered to be drugs, such as radioactive markers and contrast substances, all of which are designed to be considered to be bio-active compounds because they have an effect or application on or within a living organism.

Carbohydrate moieties of glycoproteins are known to play an important role in absorption, transport, and subsequent tissue distribution in the body, and several researchers have previously addressed the delivery problem by administering sugars in conjunction with bioactive materials. Significant results have already been achieved in this area. One study demonstrated that intestinal absorption of poorly absorbed drugs was greatly increased by glycosylating the drug with a sugar. Mizuma, T., et al., Intestinal Active Absorption of Sugar-Conjugated Compounds by Glucose Transport System: Implication of Improvement of Poorly Absorbable Drugs, *Biochem. Pharma.*, 43(9) 2037–2039 (1992). Another study identified differential targeting of different saccharide-poly-L-lysine conjugates, reporting that galactose conjugates preferentially target the liver, mannose and fucose conjugates preferentially target the reticuloendothelial system, and xylose conjugates preferentially target liver and lung. Gonsho, A., et al., Tissue-Targeting Ability of Saccharide-Poly(L-Lysine) Conjugates, *Biol. Pharm. Bull.*, 17(2) 275–282 (1994).

The research in this area breaks down into three general categories: (1) therapy in which the sugar is not bound in any manner to the bio-active compound; (2) compositions in which the sugar is covalently bound either directly or indirectly through a glycosidic bond (engaging the $C_1$ atom of the sugar) to the bio-active compound; and (3) compositions in which the drug is associated with an amphiphile, such as enclosure within a sugar coated liposome.

Development in the first category has largely involved the use of mannitol to overcome the blood brain barrier. Concentrated solutions of mannitol, for example, have been infused into the carotid arteries to disrupt the blood brain barrier long enough to allow methotrexate and other potent chemotherapeutic agents to penetrate brain tumors. Angier, N., *Discover*, May 199, 67–72. While significant results have been reported with this approach, it suffers from several drawbacks. In particular, the opening of the blood brain barrier is clearly non-specific, and permits numerous harmful compounds to enter the brain along with the desired compound. In addition, the technique targets primarily the central nervous system, and is largely inapplicable to other systems.

Developments in the second category, direct or indirect glycosidic bonding of sugars to drugs are of much greater importance. Thus, the cytotoxic drug, methotrexate (MTC) has been conjugated to mannosylated bovine serum albumin (BSA), with the resulting compound being recognized by the mannose receptors present on the surface of macrophages (Chakraborty, P. et al., Sugar Receptor Mediated Drug Delivery to Macrophages in the Therapy of Experimental Visceral Leishmaniasis, *Biochem. Biophys. Res. Comm.*, 166(1)404–410 (1990)). Insulin has been glycosylated to take advantage of the competitive binding between glucose and the glycosylated insulin (Seminoff, L. A. et al, A Self-regulating insulin delivery system. I. Characterization of a synthetic glycosylated insulin derivative, *Int'l J. Pharm.*, 54 (1989) 241–249). The anti-HIV agent, 3'-azido-3'-deoxythymidine (AZT) has also been glucosidically coupled to human serum albumin (HSA) and various sugar moieties to produce mannose-, fucose-, galactose- and glucose-neoglycoproteins (Molema, G., Targeting of Antiviral Drugs To $T_4$-Lymphocytes, *Biochem. Pharm.*, 40(12) 2603–2610 (1990)). The anti-inflammatory agent, naproxin, has also been glucosidically bound to sugar terminated HSA (Franssen, E. J. F., Hepatic and Intrahepatic Targeting of an Anti-inflammatory Agent With Human Serum Albumin and Neoglycoproteins as Carrier Molecules, *Biochem. Pharm.*, 45 (6) 1215–1226 (1993)). In the latter two cases, the glycosidic bond is formed to HSA, and thus only indirectly to the drugs, AZT or naproxin. In 1994 a Japanese group reported on a method of radioiodinating digoxin using glycosides (Takemuru, Y., et al., Development of Glycoside-Bound Radiopharmaceuticals: Novel Radioiodination Method for Digoxin, *Biol. Pharm. Bull.*, 17(1)97–101 (1974)). Sugars have also been covalently linked to pol-L-lysine by a glycosidic bond (Monsigny, M., et al., Sugar Specific Delivery of Drugs, Oligonucleotides and Genes, *Targeting of Drugs*, 4 31–50 (Ed. by G. Gregoriadis et al., Putnam Press, N.Y., 1994)).

In addition to these synthetic sugar conjugates There are numerous examples in nature of the covalent bonding of a sugar to a biologically active moiety. Glycosides, for example, are condensation products of sugars with various kinds of organic hydroxy (or occasionally amino or thiol) compounds, in which the OH of the hemiacetal portion of the carbohydrate participates in the condensation (Remington, *The Science and Practice of Pharmacy*, 19th ed. 386–387 (Mack Publ., Co., Easton, Pa., 1995)). Indeed, many well-known biologically active compounds are glycosides, including amygdalin, cymarin, digitoxin, ouabain, rutin, and salicin. There are also endogenous glycosides including gangliosides, sugar nucleotides and neural cell adhesion molecules. Other naturally occurring compounds not usually classified as glycosides actually contain glycosidic linkages in their structures. Examples include the antibiotics, gentamycin, amikacine, netilmycin, tobramycin, novobiocin and streptomycin, glucoalkaloids such as solanine, and nucleosides, which consist of a purine or pyrimidine base linked with D-ribose of D-2-deoxyribose.

As demonstrated by the usefulness of both natural and synthetic compounds, covalent direct or indirect glycosidic bonding of sugars to drugs is a successful strategy for delivery of the drugs. Despite the extensive occurrence and knowledge regarding sugar-coupled bio-active compounds, however, the compounds which can be developed by through use of the standard glycosidic bond is limited. For example, in some cases such linkage is entirely unsuitable because the size and steric hindrance of the resulting conjugated compound may no longer be recognized or properly transported by the respective cellular transporters. In other cases, glycosidic bonds are too labile and are easily hydrolyzed by glycosidases.

With respect to the third category, it is known that glycoside-bearing liposomes can be used in vivo to deliver drugs specifically to macrophages (Medda, S. et al., Sugar-coated Liposomes: a Novel Delivery System for Increasing Drug Efficacy and Reduced Drug Toxicity, *Biotechnol. Appl. Biochem.*, 17 37–47 (1993)). Anionic amphiphiles with a phosphate ester junction between a fluorophilic-lipophilic tail and a sugar-based hydrophilic head have also been synthesized (Guillod, F., et al., Amphiphilic Sugar Phosphates with Single or Double Perfluoro-alkylated Hydrophobic Chains for Use in Oxygen and Drug Delivery Systems, *Art. Cells, Blood Subs., and Immob. Biotech.*, 22(4)1273–1279 (1994)). In 1995 a scholarly analysis of the function of liposomes with surface glycolipids was published (Jones, M., The Surface Properties of Phospholipid Liposome Systems and Their Characterization, *Advances in Colloid and Interface Science*, 54 93–128 (1995)). However, this third category of compounds, while it appears promising, suffers from the same drawbacks as the glycosides and neoglycoproteins discussed above. The standard glycosidic linkage from which all of these compounds are made is too limiting. In addition, there are constant synthetic and/or purification problems in creating stereochemically pure, α- or β-glycosidic bonds.

Given the shortcomings of currently-available methods and compositions for improving cellular uptake and targeting such as uptake to specific tissues, it is of interest to provide new methods and compositions for bonding sugars to biologically active compounds.

III. SUMMARY OF THE INVENTION

Methods and compositions are provided which increase the cellular uptake of bioactive materials by covalently bonding such compounds to carbohydrate moieties through chemical linkers using non-glycosidic bonds. Numerous carbohydrates, linkers and bioactive materials can be joined in this way to form novel compositions, which are collectively referred to herein as glinkosides. Preferred glinkosides are preferentially taken up by glucose receptors and/or other monosaccharide cellular receptors, and once inside the cells, the glinkosides are cleaved into a sugar derivative, a linker or linker fragments, and a biologically active compound. Various aspects of the invention include glinkoside compositions, processes for synthesizing glinkosides, and methods of treating diseases using glinkosides.

A. BRIEF DESCRIPTION OF THE DRAWINGS

Figure 1:
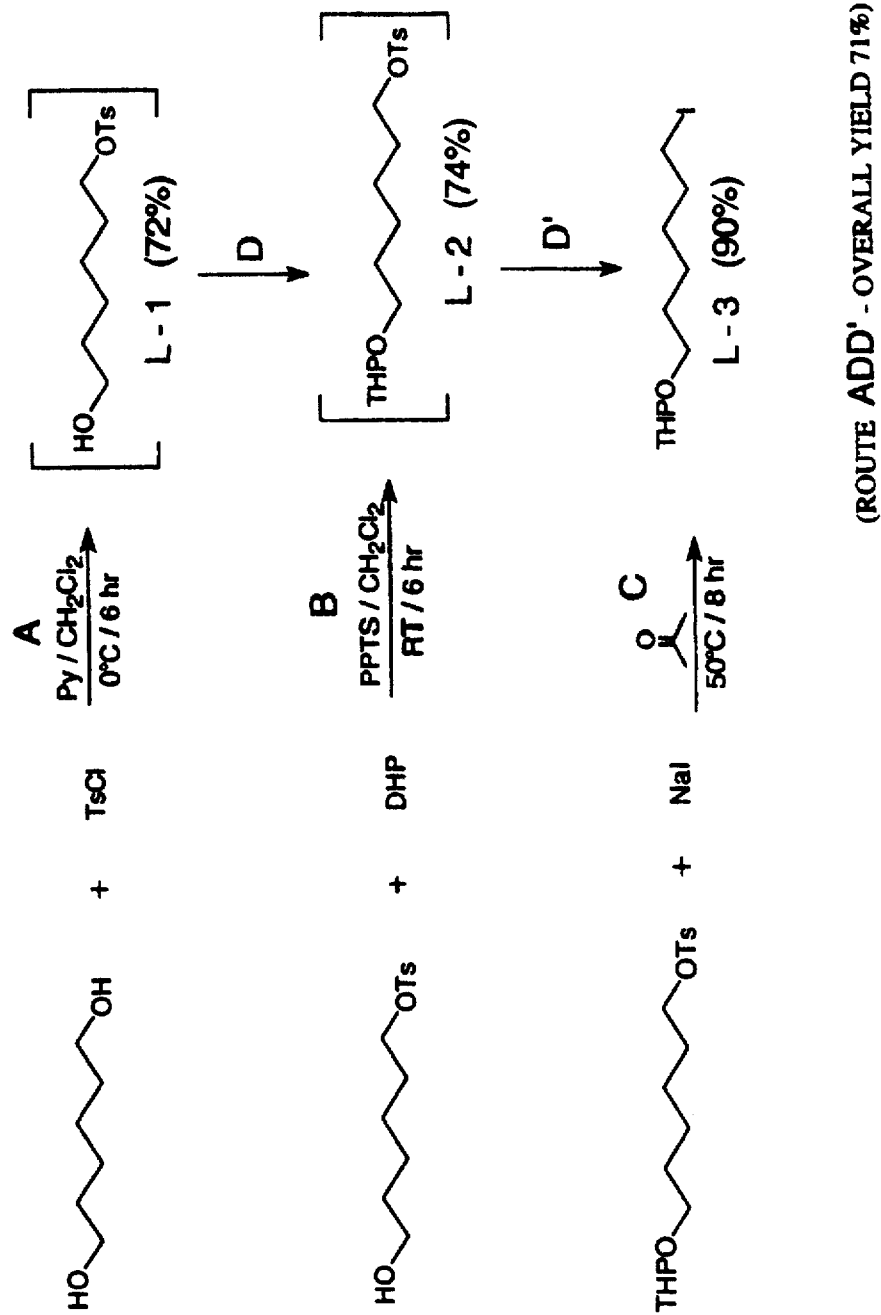

FIG. 1 outlines an exemplary synthesis of derivatized linkers.

FIG. 2 outlines an exemplary synthesis of 3-O- and 6-O-D-Galactose-Linker Intermediates.

Figure 3:
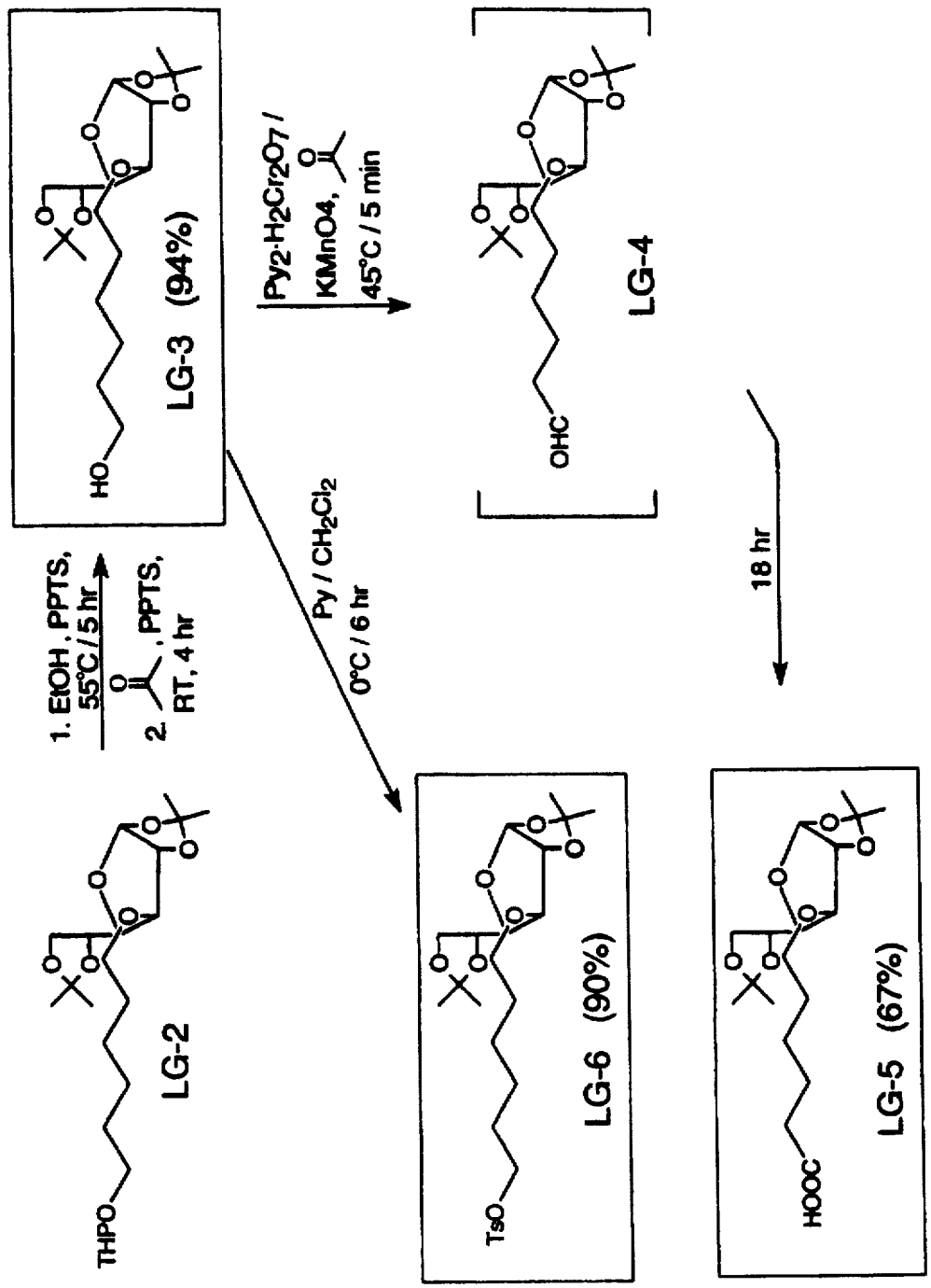

FIG. 3 outlines an exemplary synthesis of 3-O- and 6-O-D-Galactose-Linker Reactive Intermediates.

Figure 4:
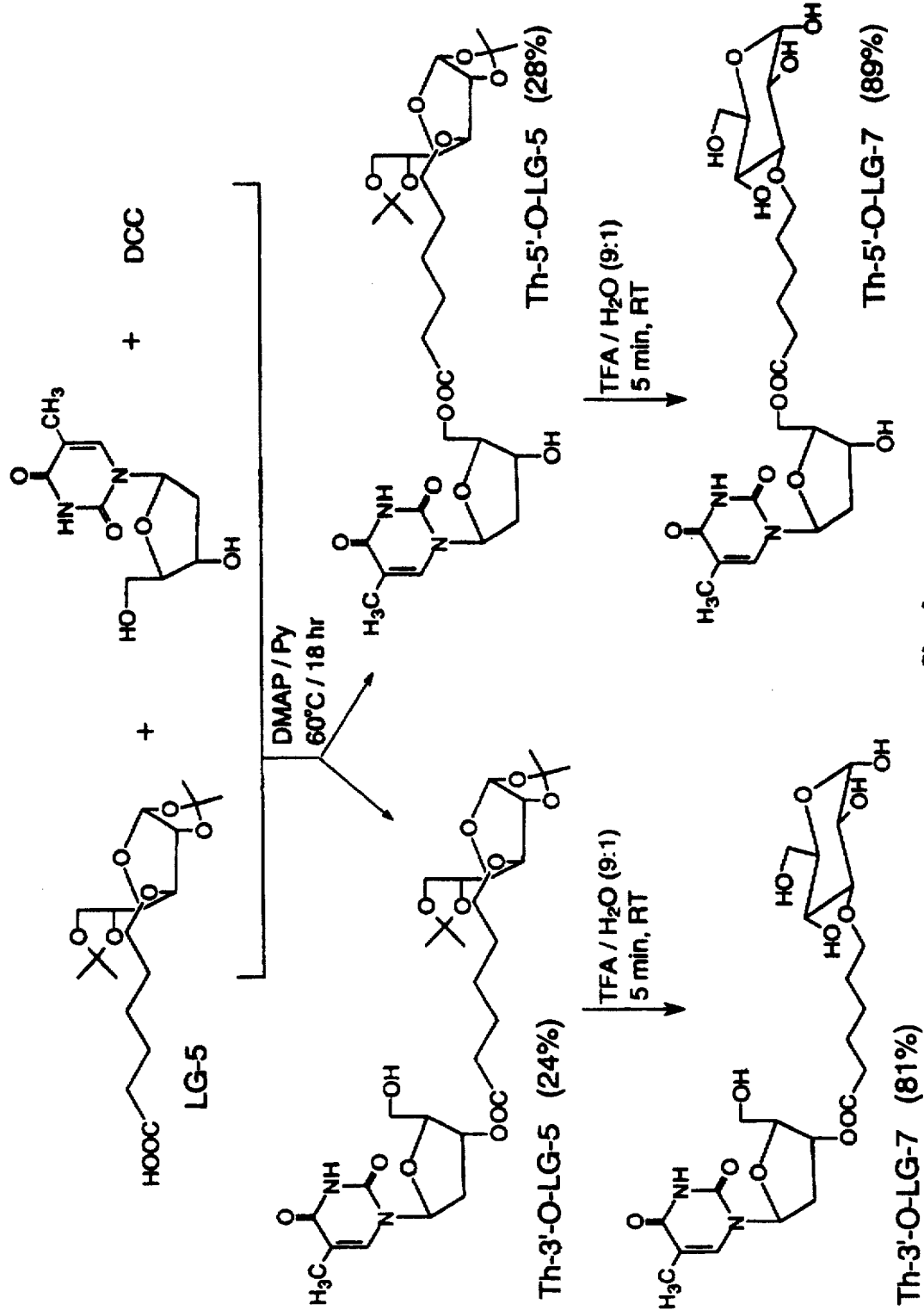

FIG. 4 outlines an exemplary synthesis of Thymidine Conjugates with LG-5 via an ester bond.

Figure 5:
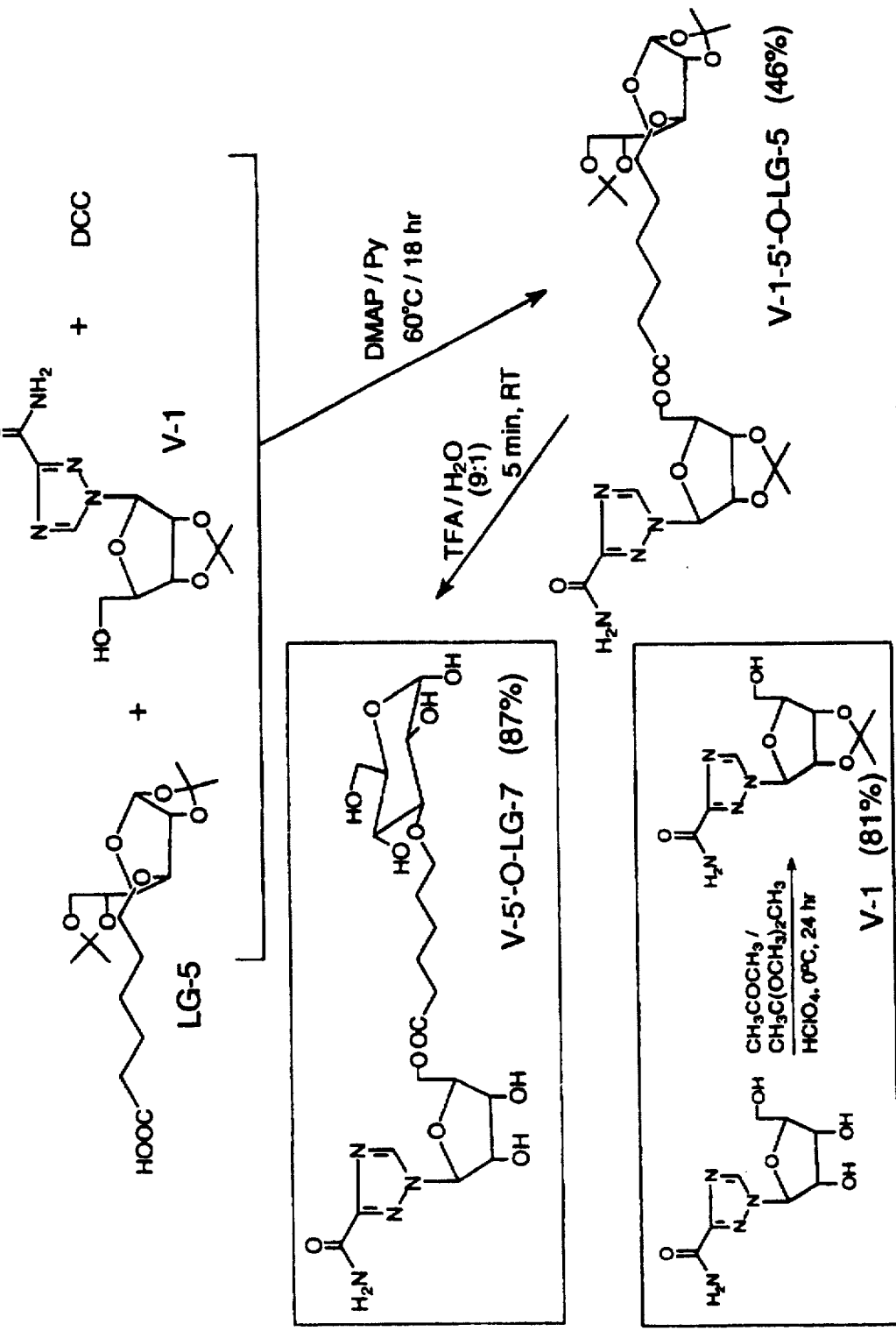

FIG. 5 outlines an exemplary Virazole™ conjugation with LG-5 via an ester bond.

Figure 6:
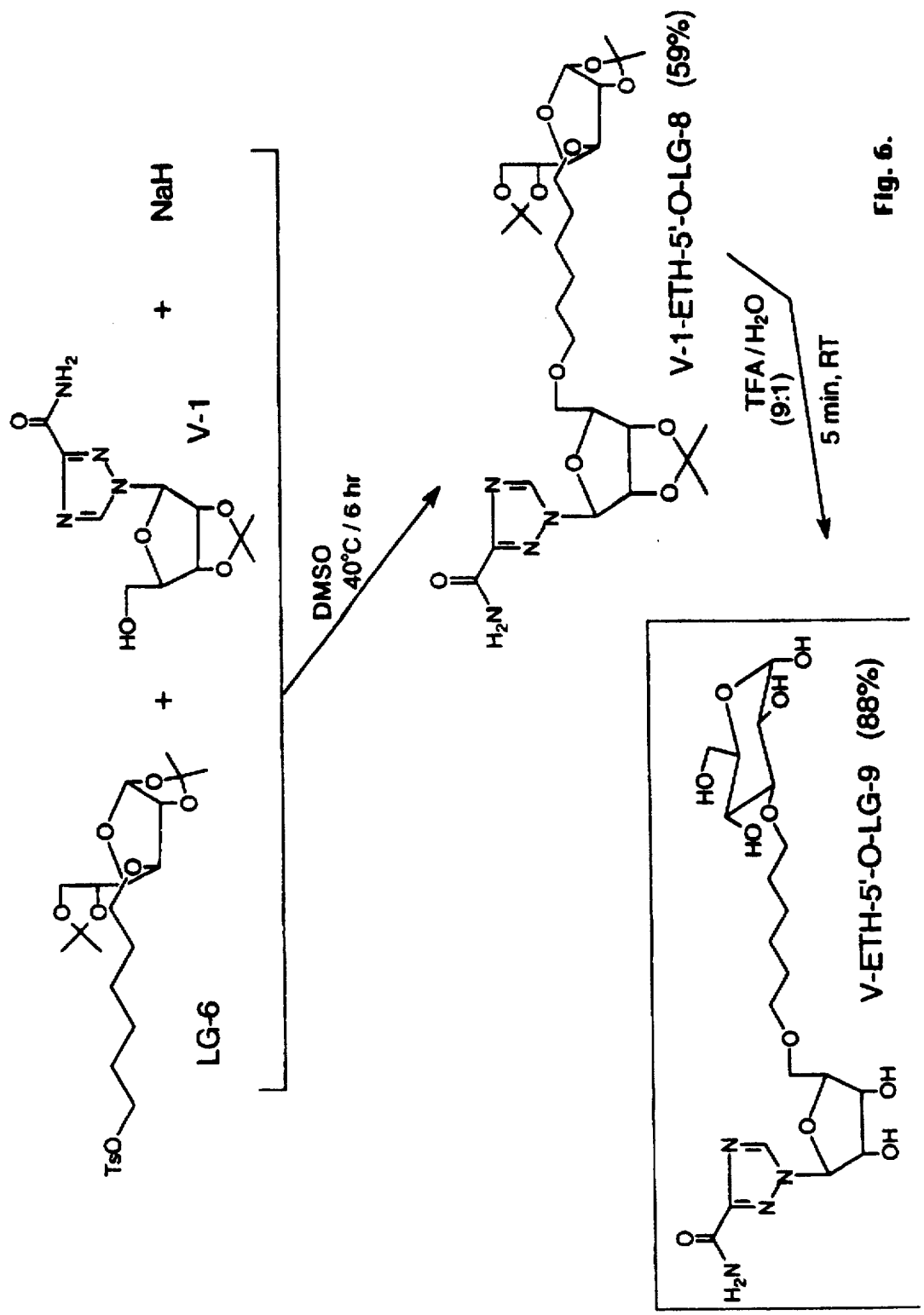

FIG. 6 outlines an exemplary Virazole™ conjugation with LG-6 via an ether bond.

FIG. 7 outlines an exemplary synthesis of 6-O-D-Galactose-Linker Intermediates.

Figure 8:
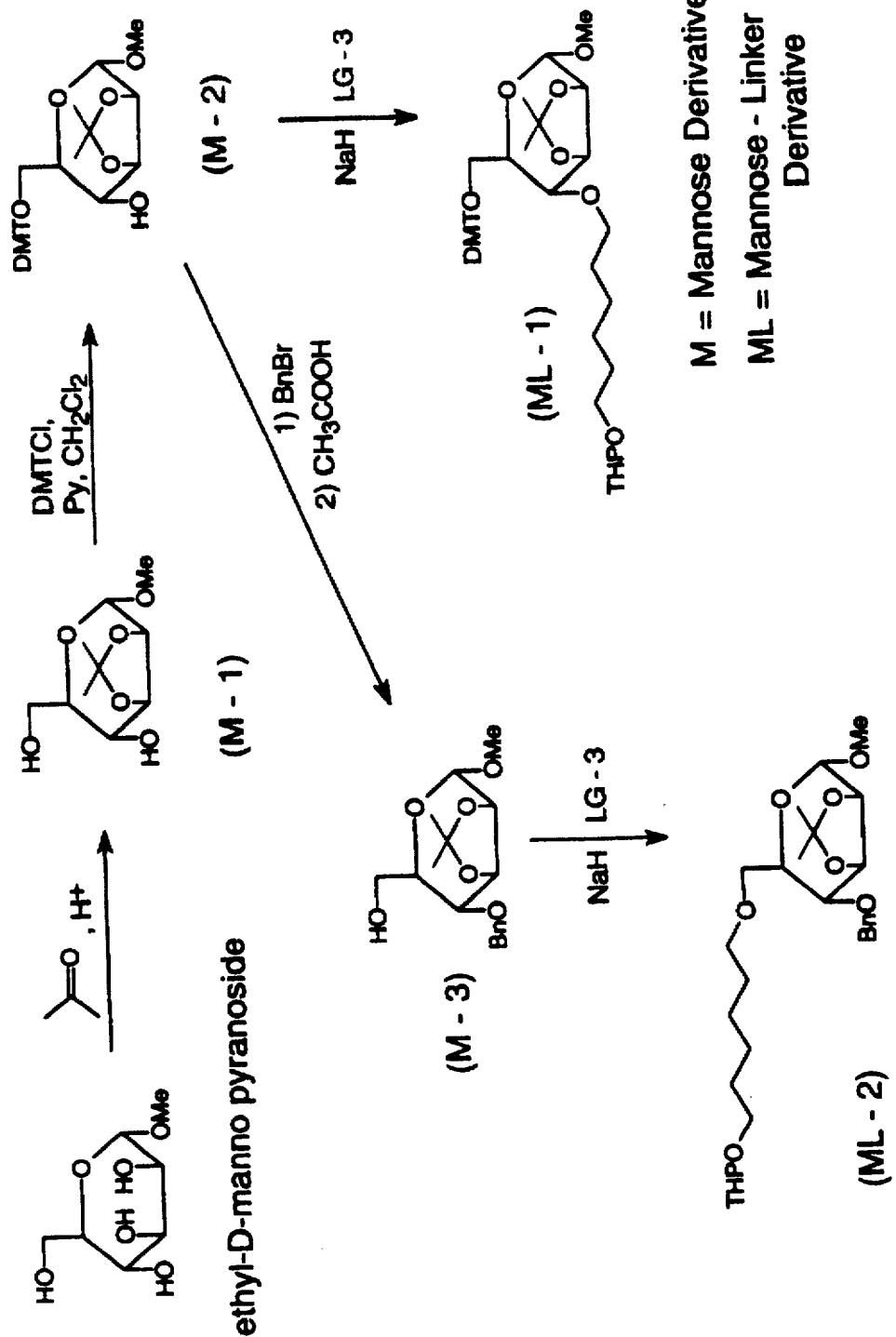

FIG. 8 outlines an exemplary synthesis of 4-O- and 6-O-D-Mannose-Linker Intermediates.

Figure 9:
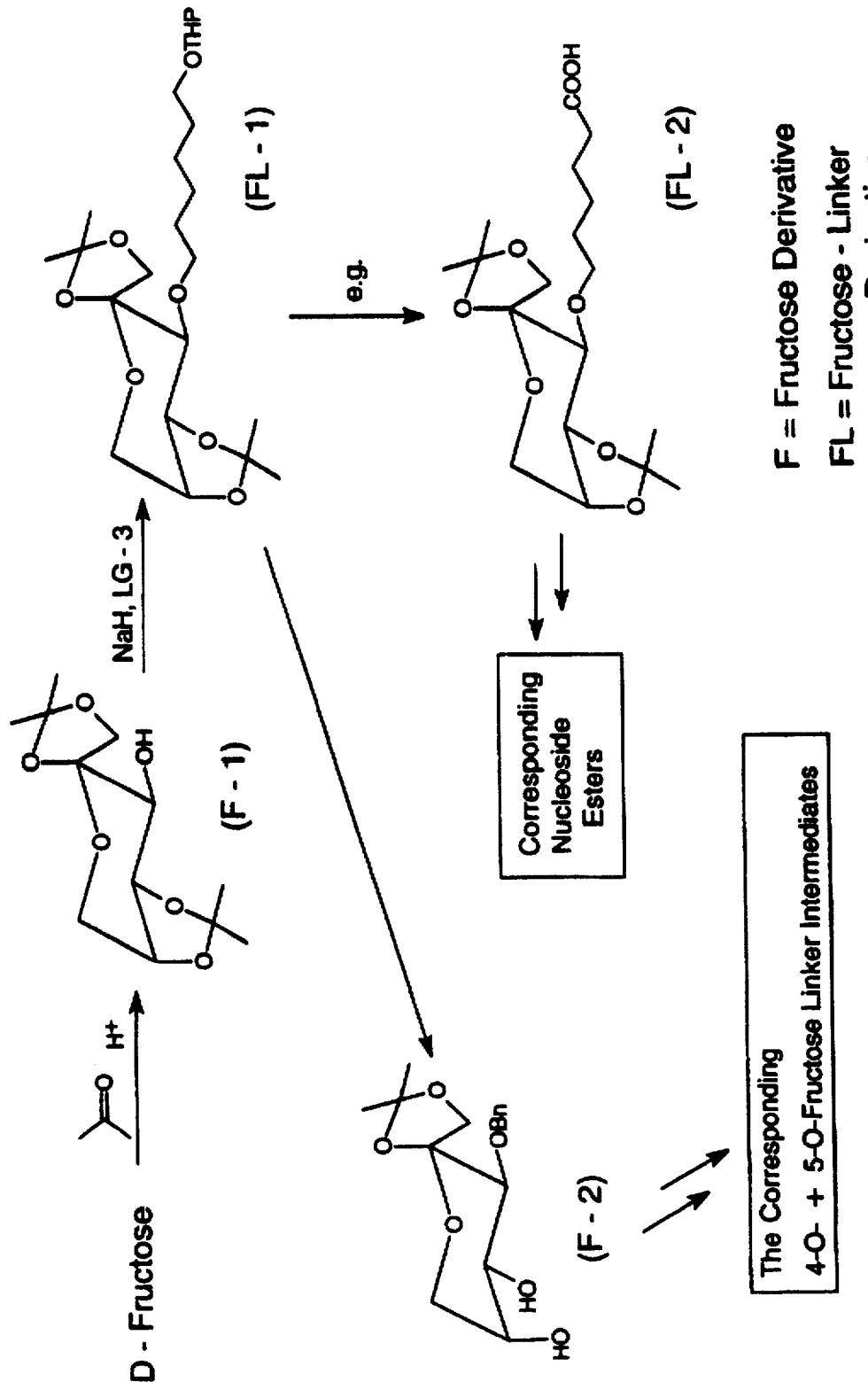
Figure 18:
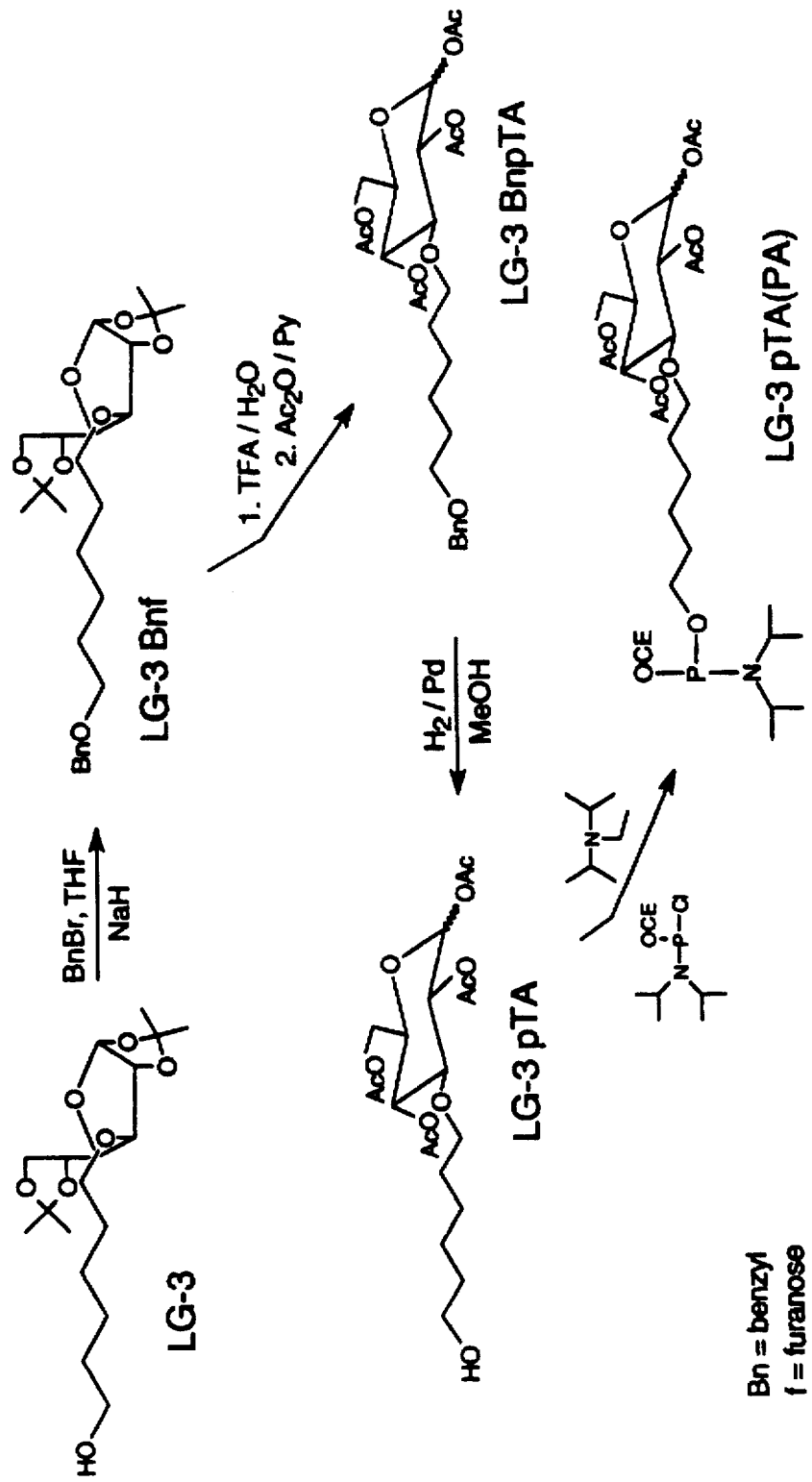

FIG. 9 outlines an exemplary synthesis of 3-O-, 4-O- and 5-O-D-Fructose-Linker Intermediates.

FIG. 10 outlines an exemplary synthesis of glucose-Linker phosphoramidate intermediates for automated oligodeoxynucleotide synthesis.

Figure 11:
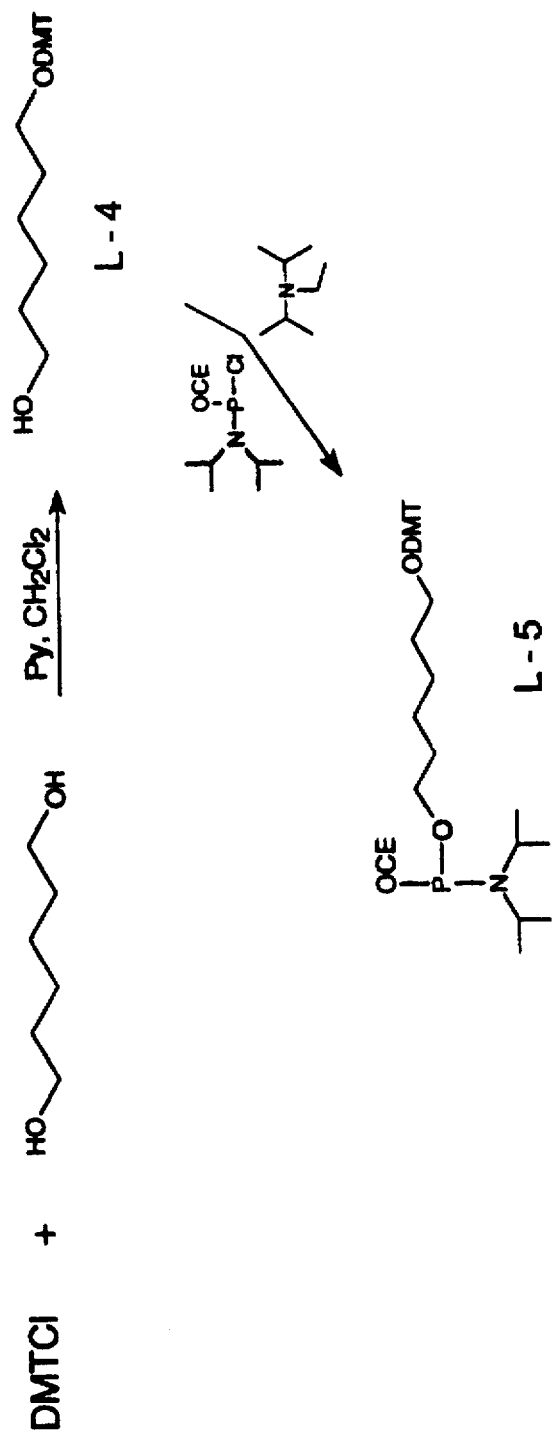

FIG. 11 outlines an exemplary synthesis of derivatized linker phosphoramidates for automated oligodeoxynucleotide synthesis.

IV. DETAILED DESCRIPTION

According to the new terminology employed herein, glinko-sides have the general structure of MS-LINK-BAM, where MS is a monosaccharide, LINK is a linker, BAM is a bioactive material. MS is covalently bound to LINK at a position other than the MS $C_1$, and LINK is covalently linked to BAM. There are a very large number of glinkoside permutations. For example, any mono-saccharide can be used in a glinkoside, including monosaccharide having from three to eight or more carbons. The LINK portion of a glinkoside is also subject to great variation, and can be straight or branched alkyl, substituted alkyl, aralkyl, substituted aralkyl, aryl, and substituted aryl. The BAM portion can consist of any bioactive molecule, including the following:

gastrointestinal and liver drugs
hematologic drugs
cardiovascular drugs
respiratory drugs
sympathomimetic drugs
cholinomimetic drugs
adrenergic and adrenergic neuron blocking drugs
antimuscarinic and antispasmodic drugs
skeletal muscle relaxants
uterine and antimigrane drugs
hormones
general and local anesthetic drugs
sedative and hypnotic drugs
antiepileptic drugs
psychopharmcologic agents
antiinflammatories
CNS stimulants.

Suitable MS-LINK and LINK-BAM bonds also vary widely, and by way of example may independently consist of ether, ester, amide, disulfide, hemiacetal, hemiketal, acetal, and ketal bonds.

Presently preferred glinkosides utilize naturally occurring ribose (5 carbon) or hexose (6 carbon) sugars, four to sixteen carbon straight chain linkers, bifunctional α,ω linkers such as hexane, and known bio-active drugs. The MS-LINK and LINK-BAM bonds are each preferably clearable under physiologic conditions such that a glinkoside acts as a prodrug, delivering an active or activatable drug to a target position on or within a target cell. Presently preferred embodiments involve glinkosides in which the LINK-SAM bond is stronger than the MS-LINK bond.

Glinkosides have numerous advantages over glycosides, including the following:

(1) The monosaccharide can be chemically bonded through a specifically designed α,ω bifunctional linker to a BAM at any of the different OH substituents (except $C_1$) found on the monosaccharide.

(2) Use of a linker can eliminate synthetic stereochemical problems.

(3) Relative to glycosides, and particularly glycosides in which the SAM is directly attached to the monosaccharide, steric hindrance is largely or entirely eliminated. This facilitates passage of the glinkoside through specific membrane protein transporters such as one of the glucose transporter systems. The glutamine transporter system (GLUT-1) is an example of such a system.

(4) The relative strengths of the monosaccharide-linker and linker-BAM bonds can be varied so that the BAM can be released at an appropriate point in the transport.

(5) Glinkosides also offer enhanced passage across the blood-brain barrier.

Synthesis of Glinkosides

In order to chemically connect carbohydrates to bio-active compound(s), selected functional groups in both chemical entities may be used to covalently bind them through a specific chemical linker. Quite often functional groups in carbohydrates and bioactive materials involve: hydroxy-, amino-, mercapto-, carbonyl-, carboxyl-, and amido- functions. Chemical linkers in most cases comprise alpha, omega difunctional alkyl chains. Obviously there are many more functional groups and chemical bonds available for this particular purpose.

In general, glinkosides can be prepared using the following steps: (1) Prepare an appropriate linker. In the case of a bifunctional α,ω linker, the α-end would be reactive and the ω-end would be protected; (2) Select a monosaccharide and chemically bind one of its non-$C_1$ —OH groups to the linker; and (3) Chemically bind the linker to a bio-active material. Exemplary synthetic methods and glinkoside compounds are disclosed in the examples below. It should, of course, be appreciated that the examples presented are illustrative only, and are not intended to delimit the scope of the invention.

Synthesis of Derivatized Linkers

In FIG. 1, the first row shows an exemplary synthesis of 1-0-p-Toluene sulfonyl-1,6-hexane diol (L-1) using the following reagents: 1,6-Hexane diol=1,6-HD; p-Toluene sulfonyl chloride=TsCl; Pyridine=Py; and Dichloro methane= $CH_2Cl_2$. In that procedure, 6-HD (44 g, 0.372 mol) was dissolved in Py/$CH_2Cl_2$ (1:1) mixture (80 ml). The resulting solution was cooled to 0° C., and TsCl (20 g, 0.105 mol) was added. The obtained reaction mixture was kept at 4° C. for 5 hours. The reaction solution was then neutralized with 10% aq. HCl and product was extracted by $CH_2Cl_2$ (3×100 ml). The organic layer was washed with brine, dried and evaporated. The crude product was purified by flash chromatography on a silica gel column (using TLC solvent system). L-1 (oil); Yield: 20.6 g (72%). TLC: Ethyl acetate/Hexane (1:1); Rf: 0.56. Structure and purity of L-1 were checked by $^1$H-NMR spectrum.

The second row shows an exemplary synthesis of 1-O-p-Toluene sulfonyl-6-O-(2'-tetrahydropyranyl)-1,6-hexane diol (L-2) using the following reagents: L-1; Dihydropyrane=DHP; Pyridinium p-toluene sulfonate= PPTS (prepared from pyridinium (Py) and p-Toluene sulfonic acid=TsOH); and $CH_2Cl_2$. In this procedure L-1 (10 g, 36.7 mmol), DHP (3.4 g, 40.3 mmol) and PPTS (1.0 g, 3.7 mmol) were added one by one to anhydrous $CH_2Cl_2$ (40 ml). The reaction mixture was stirred at room temperature until the reaction was completed (6–8 hours). The reaction mixture was washed with brine (3×20 ml), dried and evaporated. Crude product was purified by silica gel column chromatography (using TLC solvent system). (L-2 (oil); Yield: 9.42 g (72%). TLC: 15% Ethyl acetate, 1% triethyl amine in Hexane; Rf=0.9; Structure and purity of L-2 were checked by $^1$H-NMR-spectrum.

The third row shows an exemplary synthesis of 1-O-(2'-tetrahydropyranyl)-6-iodo-1-hexanol (L-3) using the following reagents: L-2; NaI; and Acetone. In this procedure, a mixture of L-2 (9.0 g, 25.2 mmol), NaI (11.3 g, 75 mmol) and dry acetone (100 ml) was stirred at 50° C. until the reaction was completed (8–12 hours). Acetone was evaporated and the residue was treated with water (100 ml). The product was extracted with $CH_2Cl_2$ (3×50 ml). The organic layer was washed with brine (3×50 ml), dried and evaporated. The product was collected by silica gel column chromatography (TLC solvent system). L-3 (oil); Yield: 5.0 g (63%). TLC: 5% Triethyl amine in Hexane; Rf: 0.50; $^1$H-NMR-spectrum (CDCl$_3$) confirms the structure and purity of L-3.

EXAMPLE 4

Synthesis of 3-O- and 6-O-D-Glucose-Linker Intermediates

FIG. 2 shows an exemplary synthesis of 1,2-O-Isopropylidene-3-O-(6'-tetrahydropyranyloxy)-hexyl-alpha-D-glucofuranose (LG-1.a) and 1,2-O-Isopropylidene-6-O-(6'tetrahydropyranyloxy)-hexyl-alpha-D-glucofuranose (LG-1b) using the following reagents: L-3; 1,2-O-Isopropylidene-alpha-D-glucofuranose=IPGF; NaH; and Dimethyl sulphoxide=DMSO. In this procedure, IPGF (2.0 g, 9.08 mmol) was dissolved in anhydrous DMSO (7 ml) and NaH (total of 545 mg, 13.6 mmol) was added in several small portions at room temperature. The reaction mixture was kept at 40° C. for 0.5 hour and L-3 (2.27 g, 7.26 mmol) was added. The resulting mixture was kept at room temperature overnight and then poured onto ethyl acetate (200 ml). Organic layer was washed with brine (3×50 ml), dried (anh. Na$_2$SO$_4$) and evaporated. Crude product mixture was purified and the isomers were separated by flash chromatography on a silica gel column (TLC solvent system). LG-1a (oil); Yield: 1.06 g. (36%), and LG-1b(oil); Yield: 0.94 g. (32%). TLC: 50% Ethyl acetate, 2.5% Triethyl amine, 47.5% Hexane; Rf (LG-1a): 0.34; Rf (LG-1b): 0.47. $^1$H-NMR spectra of both isomers in CDCl$_3$ are in accordance with the proposed structures (samples were chemically pure).

EXAMPLE 5

1,2:5,6-Di-O-Isopropylidene-3-O-(6'-Tetrahydropyranyloxy)-Hexyl-Alpha-D-Glucofuranose (LG-2)

FIG. 2 also shows an exemplary synthesis of 1,2:5,6-di-O-isopropylidene-3-O-(6'-tetrahydropyranyloxy)-hexylalpha-D-glucofuranose (LG-2) using the following reagents: LG-1a; Acetone; and PPTS (prepared from TsOH and Py). In this procedure a mixture of LG-1a (500 mg, 1.233 mmol), PPTS (67 mg, 0.247 mmol) and acetone was stirred at room temperature until the reaction was completed (6 hours). Acetone was evaporated and residual material was chromatographed. LG-2 (oil). Yield: 490 mg (91%). TLC: 15% ethyl acetate, 5% triethyl amine, hexane 80% Rf: 0.66. $^1$H-NMR-spectrum (CDCl$_3$) confirms the purity and structure of LG-2.

EXAMPLE 6

Alternative Synthesis of 1,2:5,6-Di-O-Isopropylidene-3-O-(6,-Tetrahydropyranyloxy)-Hexyl-Alpha-Glucofuranose An alternative direct synthesis of LG-2 may be performed using the following reagents: 1,2:5,6-di-O-isopropylidene-alpha-D-glucofuranose=DIPGF L-3; NaH; and DMSO. In this procedure DIPGF (2.5 g, 9.6 mmol) was dissolved in anhydrous DMSO (7 ml) and NaH (576 mg, 14.40 mmol) was added in small portions at room temperature. The reaction mixture was kept at 40° C. for 30 minutes and L-3 (3.6 g, 11.52 mmol)was added. The reaction mixture was kept overnight at room temperature and then poured into ethyl acetate (200 ml). Organic layer was washed with brine (3×50 ml), dried (Na$_2$SO$_4$) and evaporated. The product was purified by silica gel column chromatography. LG-2 (oil); Yield: 2.42 g (58%). TLC: 15% ethyl acetate, 5% triethyl amine, 80% hexane Rf: 0.66.

EXAMPLE 7

Synthesis of 3-O-D-Glucose-Linker Reactive Intermediates

FIG. 3 shows an examplary synthesis 1,2:5,6-di-O-isopropylidene-3-O-(6'-hydroxy)-hexyl-alpha-D-glucofuranose (LG-3) using the following reagents: LG-2; Ethanol(96%); PPTS and Acetone. In this procedure LG-2 (2.0 g, 4.49 mmol) and PPTS (245 mg, 0.90 mmol) were dissolved in ethanol (100 ml) and the reaction mixture was heated for 5 hours at 55° C. Ethanol was then evaporated. The residual material was dissolved in acetone (100 ml) and stirred at room temperature for the next 4 hours. After removal of acetone in vacuum, the residue was dissolved in ethyl acetate (50 ml), washed with brine (3×50 ml), dried (Na$_2$SO$_4$) and evaporated. The product was finally purified by flash chromatography on silica. LG-3 (oil); Yield: 1.52 g (94%). TLC: Ethyl acetate/Hexane (1:1); Rf: 0.48; $^1$H-NMR-spectrum confirms purity and structure of LG-3.

EXAMPLE 8

1,2:5,6-Di-O-Isopropylidine-3-O-(5'-Hydroxycarbonyl)-Pentyl-Alpha-D-Glucofuranose (LG-5)

FIG. 3 also shows an exemplary synthesis of 1,2:5,6-Di-O-isopropylidene-3-O-(5'-hydroxycarbonyl)-pentyl-alpha-D-glucofuranose (LG-5) using the following reagents: LG-3; Py$_2$H$_2$Cr$_2$O7 (Pyridinium dichromate)=PDCh; KMnO4 and Acetone. In this procedure a mixture of LG-3 (1.0 g, 2.77 mmol), PDCh (2.13 g, 5.65 mmol), KMnO$_4$ (0.89 g, 5.65 mmol) and acetone (50 ml) was stirred at 50° C. until the reaction was completed (7–8 hours). By monitoring the reaction with TLC, almost complete transformation of starting LG-3 to the intermediary aldehyde (LG-4) was observed after only 5 minutes (in a separate experiment LG-4 was isolated and its purity and structure was proved by the corresponding $^1$H-NMR-spectrum). After the oxidation to the acid LG-5 was over, the reaction mixture was filtered and the filtrate was evaporated. The product was purified by flash chromatography (TLC solvent system). LG-5 (oil); Yield: 700 mg (67%); TLC: Ethyl acetate/Hexane (1:1); Rf: 0.23; $^1$H-NMR-spectrum (CDCl$_3$) confirms the purity and structure of LG-5.

EXAMPLE 9

1,2:5,6-Di-O-Isopropylidene-3-O-(6'-p-Toluene-Sulfonyloxy)-Hexyl-Aalpha-D-Glucofuranose (LG-6)

FIG. 3 also shows an exemplary sysnthesis of 1,2:5,6-Di-O-isopropylidene-3-O-(6'-p-toluenesulfonyloxy)-hexyl-alpha-D-glucofuranose (LG-6) using the following reagents: LG-3; TsCl; Py; and CH$_2$Cl$_2$. In this procedure LG-3 (1.40 g, 3.884 mmol) was dissolved in a mixture of pyridine (5 ml) and CH$_2$Cl$_2$ (10 ml). The reaction mixture was cooled to 0° C. and TsCl (0.89 g, 4.668 mmol) was added. The reaction mixture was kept for 5 hours at 4° C. and then neutralized with aq. 10% HCl. Organic layer was washed with brine, dried and evaporated. The product was purified by column chromatography (TLC solvent system). LG-6 (oil); Yield: 1.8 g (90%); TLC: 33% Ethyl acetate, 67% Hexane; $^1$H-NMR-spectrum (CDCl$_3$) confirms the purity and structure of LG-6.

EXAMPLE 10

Thymidine Conjugates with LG-5 (Via an Ester Bond)

FIG. 4 shows an exemplary synthesis of Thymidine 3'-O- and 5'-O-esters with LG-5 using the following reagents: Thymidine; LG-5; Dicyclohexylcarbodiimide=DCC; and Dimethylamino pyridine=DMAP. In this procedure a mixture of Thymidine (100 mg, 0.413 mmol), LG-5 (233 mg, 0.620 mmol), DCC (128 mg, 0.620 mmol), DMAP (15.1 mg, 0.124 mmol) and Py (3 ml) was kept at 60° C. overnight which was sufficient for the reaction to go to completion. Py was evaporated in vacuum and residual material was chromatographed on a silica gel column (TLC solvent system). 5'-O- and 3'-O-Thymidine esters (oils); yields: 68.7 mg (28%) and 59.0 mg (24%) TLC: 25% Hexane, 75% Ethyl acetate; Rf (5): 0.40 and Rf(3): 0.25. $^1$H-NMR-spectra (CDCl$_3$) of both isomers are in accordance with the proposed structures.

EXAMPLE 11

De-Isopropylidenation (Deprotection) of Separated Thymidine Esters

FIG. 4 also shows an exemplary de-isopropylidenation (deprotection) of separated Thymidine esters using Trifluoroacetic acid=TFA. In this procedure separated (single) Thymidine ester (from a previous experiment), 30 mg, 0.05 mmol, was treated with TFA/Water (9/1, v/v) at room temperature for 5 minutes. The reaction mixture was then evaporated in vacuum, redissolved in 1 ml of water, filtrated and evaporated once again. Deprotected esters (oils); Yields: 81–89%; TLC: 10% methanol, 2% acetic Acid, 88% ethyl acetate; Rf: 0.17 (free 5'-OH) and 0.20 (free 3'-OH). $^1$H-NMR-spectra in accordance with proposed structures.

EXAMPLE 12

Virazole Conjugation with LG-5 (Via an Ester Bond)

FIG. 5 shows an exemplary synthesis of 2,3-O-Isopropylidene-virazole (V-1) using the following reagents:

Virazole™ (ICN brand name for Ribavirin USP); Acetone; 2,2-Dimethoxypropane=DMP; and Perchloric acid (70%). In this procedure Virazole™ (3.0 g, 12.28 mmol) was suspended in a mixture of acetone (40 ml) and DMP (20 ml). The mixture was cooled in an ice bath and perchloric acid (600 ul) was added. The mixture was kept at room temperature for 3 hours and then at 5° C. overnight. The resulting orange colored solution was neutralized with 2M aq. KOH, filtered and evaporated to dryness. The solid residue was treated with methanol (5 ml) and the insoluble product was removed by filtration. The methanolic filtrate was evaporated to dryness and the solid residue was recrystallized from acetone. Yield: 2.95 g (81%); TLC: 15% methanol, 85% ethyl acetate; Rf: 0.54. $^1$H-NMR-spectrum (acetone-d6) confirms the purity and structure of V-1.

EXAMPLE 13

2',3'-O-Isopropylidene-Virazole-5'-O-Ester

FIG. 5 also shows an exemplary sysnthesis of 2',3'-O-Isopropylidene-virazole-5'-O-ester with LG-5 (V-1-5'-O-LG-5) using the following reagents: V-1; LG-5; DCC; DMAP; Pyridine. In this procedure a mixture of V-1 (236 mg, 0.796 mmol), LG-5 (200 mg, 0.531 mmol), DCC (108 mg, 0.531 mmol), DMAP (13 mg, 0.106 mmol) and Py (5 ml) was kept at 60° C. overnight. Pyridine was removed in vacuum and the residue was purified by silica gel column chromatography. Yield: 160 mg (46%)TLC: 25% Hexane, 75% Ethyl acetate; Rf: 0.21. $^1$H-NMR-spectrum (acetone-d6) confirms the purity and structure of V-1-5'-O-LG-5.

EXAMPLE 14

Deprotection of V-1-5'-O-LG-5 and Synthesis of V-5'-O-LG-7

FIG. 5 also shows an exemplary deprotection of V-1-5'-O-LG-5 and synthesis of V-5'-O-LG-7 using protected Virazole™ ester from a previous experiment (V-1-ester) TFA. In this procedure V-1 ester (50 mg, 0.076 mmol) was treated with TFA/water (9/1, v/v) at room temperature for 5 minutes. The reaction mixture was evaporated to dryness, redissolved in 1 ml of water, filtrated and evaporated once again. Yield: 35 mg (87%); TLC: 10% methanol, 2% acetic acid, 88% ethyl acetate Rf: 0.19. $^1$H-NMR-spectrum (D$_2$O) confirms purity and structure of V-5'-O-LG-7.

EXAMPLE 15

Virazola™ Conjugation with LG-6 (via an Ester Bond)

FIG. 6 shows an exemplary syntheses of V-1-ETH-5'-O-: LG-8 and LG-9 using the following reagents: V-1; LG-6; NaH; and DMSO. In this procedure V-1 (250 mg, 0.843 mmol) was dissolved in anhydrous DMSO (5 ml) and NaH (118 mg, 2.95 mmol) was added in small portions during 30 minutes. The reaction mixture was heated for the next 30 minutes at 40° C. and then LG-6 was added. The mixture was kept at room temperature overnight and then was diluted with 100 ml of ethyl acetate. The solution was washed with brine (3×30 ml), dried (Na$_2$SO$_4$), evaporated and purified by silica gel column chromatography. Yield: 220 mg (49%); TLC:10% Hexane, 90% Ethyl acetate; Rf: 0.53; $^1$H-NMR-spectrum (acetone-d6) supports the proposed structure.

EXAMPLE 16

Virazole™ Conjugation with LG-6 (Via an Ester Bond)

In another exemplary synthesis the previous compound (50 mg, 0.078 mmol) was treated with TFA/water (9/1, v/v) at room temperature for 5 minutes. The reaction mixture was evaporated to dryness, redissolved in 1 ml of water, filtrated and again evaporated. Yield of V-ETH-5'-O-LG-9: 36 mg (88%); TLC: 10% methanol, 2% acetic acid, 88% ethyl acetate.

EXAMPLE 17

Synthesis of 6-O-D-Galactose-Linker Intermediates

FIG. 7 shows an exemplary synthesis of 1,2:3,4-Di-O-isopropylidene-6-O-(6'-tetrahydropyranyloxy)-hexyl-alpha-D-galactopyranose (LGa-2) using the following reagents: L-3; 1,2:3,4-Di-O-isopropylidene-alpha-D-galactopyranose=DIPGap; NaH; and DMSO. In this procedure DIPGap (500 mg, 1.92 mmol) was dissolved in anhydrous DMSO (5 ml) and NaH (96 mg, 2.40 mmol) was added in small portions at room temperature. The reaction mixture was heated at 40° C. for 0.5 hour and L-3 (660 mg, 2.11 mmol) was added at room temperature. The mixture was kept at room temperature overnight and then poured into 100 ml of ethyl acetate. Organic layer was washed with brine (3×25 ml), dried (Na$_2$SO$_4$) and evaporated. The product was purified by flash chromatography on silica (solvent system: 10% ethyl acetate, 2.5% triethyl amine, 87.5% Hexane). Yield: 500 mg (62%); TLC: 15% ethyl acetate, 2.5% triethyl amine, 82.5% hexane; Rf: 0.44. $^1$H-NMR-spectrum (CDCl$_3$) confirms the purity and structure of LGa-2. LGa-1 was obtained in a similar procedure as LG-3 (See FIG. 3).

EXAMPLE 18

Synthesis of 4-O- and 6-O-D-Mannose-Linker Intermediates

FIG. 8 shows the synthesis of 4-O- and 6-O-D-mannose-linker intermediates. The synthesis is carried out using chemistry similar to that described previously for galactose and glucose.

EXAMPLE 19

Synthesis of 3-O-, 4-O- and 5-O-D-Fructose-Linker Intermediates

FIG. 9 shows the synthesis of 4-O- and 6-O-D-mannose-linker intermediates. The synthesis is carried out using chemistry similar to that described previously for galactose and glucose.

EXAMPLE 20

Glucose-Linker Phosphoroamidate Intermediates for the Automatic Oligodeoxynucleotide (ODN) Synthesis FIG. 10 shows an exemplary synthesis of LG-3 Bnf using the following reagents: LG-3; Benzyl bromide=BnBr; Sodium hydride=NaH; and Tetrahydrofuran=THF. In this procedure a mixture of LG-3 (1.00 g, 2.77 mmol) and NaH (150 mg, 3.75 mmol) in THF (10 ml) was stirred at 40° C. for 1 hour followed by an addition of BnBr (1.3 ml, 11.08 mmol). The reaction mixture was further stirred at 40° C. until reaction was completed (6 hours). Ethyl acetate (100 ml) was then added and the obtained solution was washed with brine (3×50 ml). Organic layer was dried (Na$_2$SO$_4$) and evaporated. The product was purified by silica gel flash chromatography (TLC solvent system). Yield: 1.25 g (94%); TLC:15% Ethyl acetate, 85% Hexane; Rf: 0.45. $^1$H-NMR-spectrum (acetone-d6) is in accordance with the proposed structure.

EXAMPLE 21

LG-3BnpTA

FIG. 10 also shows an exemplary synthesis of LG-3BnpTA using the following reagents: LG-3 Bnf; Trifluoroacetic acid=TFA; Acetic anhydride=Ac2O; and Pyridine=Py. In this procedure, LG-3Bnf (1.00 g, 2.22 mmol) was treated with a 4 ml TFA/Water (9:1, v/v) at room temperature for 7 minutes. The reaction mixture was evaporated in vacuum to dryness, redissolved in Ac2O/Py mixture (10 ml, 1:1, v/v) and left at room temperature overnight. After neutralization (5% aq. HCl, 50 ml) the product was extracted with ethyl acetate (3×50 ml). Organic layer was washed with brine (3×50 ml), dried ($Na_2SO_4$) and evaporated. The product was finally purified by flash chromatography on a silica gel column (TLC solvent system). Yield: 1.15 g (96%); TLC: 33% Ethyl acetate, 67% Hexane; Rf: 0.44. $^1$H-NMR-spectrum (acetone-d6) confirms the purity and structure of LG-3BnpTA.

EXAMPLE 22

LG-3pTA

FIG. 10 also shows an exemplary synthesis of LG-3pTA using the following reagents: LG-3BnpTA; 10% Pd/C; and Methanol. In this procedure LG-3BnpTA (1.00 g, 1.86 mmol) was dissolved in methanol (50 ml) and then the catalyst (Pd/C, 200 mg) was added. The reaction mixture was shaken in H2-atmosphere until the reaction was completed (18–24 hours). Catalyst was then removed by filtration and the methanolic solution was evaporated to dryness. The product was purified by flash chromatography on silica. Yield: 815 mg (98.1%); TLC: Ethyl acetate/Hexane (1/1) Rf: 0.21; $^1$H-NMR-spectrum ($CDCl_3$) is in accordance with the proposed structure.

EXAMPLE 23

LG-3pTAPA

FIG. 10 also shows an exemplary synthesis of the phosphoroamidate intermediate, LG-3pTAPA, using the following reagents: LG-3pTA; Chloro-Cyanoethyloxy-Diisopropylamino-Phosphine=PAP (Phosphoroamidate Precursor); Diisopropylethyl amine=DIPEA; and $CH_2Cl_2$. In this procedure LG-3pTA (300 mg, 0.669 mmol) was dissolved in $CH_2Cl_2$ (3 ml) under argon. The resulting solution was cooled to 0° C. and DIPEA (450 ul, 2.62 mmol) was added. After 15 minutes PAP (315 ul, 1.408 mmol, 0° C.) was added, too. The obtained reaction mixture was kept at room temperature for the next two hours, then cooled (0° C.), diluted with cold $CH_2Cl_2$ (100 ml), washed with cold 5% aq. $NaHCO_3$, dried ($Na_2SO_4$) and evaporated in vacuum. Crude product was purified by flash chromatography on silica. The pure product was kept under argon prior to its use in an automatic oligodeoxynucleotide synthesis. For the automatic ODN synthesis, LG-3pTAPA was used as a 0.1M solution in anhydrous acetonitrile. Yield: 257 mg (62.2%); TLC: 32% Ethy acetate, 5% Triethyl amine, 63% Hexane; Rf: 0.53. $^{31}$P-NMR-spectrum was in accordance with the proposed structure.

EXAMPLE 24

Derivatized Linker Phosphoroamidates for Automatic Oligodeoxynucleotide Synthesis FIG. 11 shows an exemplary synthesis of L-4 using the following reagents: 1,6-Hexanediol=HD; and Dimethoxytrytyl chloride=DMT-Cl. In this procedure HD (4.00 g, 29.52 mmol) was dissolved in $Py/CH_2Cl_2$ (1:1, v/v) mixture (8.0 ml). The resulting solution was cooled to 0° C. and DMT-Cl (2.50 g , 7.38 mmol) was added. The obtained reaction mixture was kept at 4° C. for 6 hours. Reaction solution was then carefully neutralized (pH8) with 5% aq HCl and the product was extracted with $CH_2Cl_2$ (3×50 ml). Organic layer was washed with brine (3×30 ml), dried ($Na_2SO_4$) and evaporated. Crude product was purified by flash chromatography on silica. Yield: 2.53 g (81.5%); TLC: 32% Ethyl acetate, 3% Triethyl amine, 65% Hexane; Rf: 0.38; $^1$H-NMR-spectrum is in accordance with the proposed structure.

EXAMPLE 25

L-5

FIG. 11 also shows an exemplary synthesis of L-5 using the following reagents: L-4; PAP; and DIPEA. In this procedure L-4 (500 mg, 1.19 mmol) was dissolved in $CH_2Cl_2$ (5 ml) under argon. The resulting solution was cooled to 0° C. and DIPEA (800 ul, 4.65 mmol) was added. After 15 minutes PAP (550 ul, 2.46 mmol) was added, too. The obtained reaction mixture was kept at room temperature for the next two hours, then cooled (0° C.), diluted with cold $CH_2Cl_2$ (100 ml), washed with cold 5% aq. $NaHCO_3$, dried ($Na_2SO_4$, $NaHCO_3$) and evaporated in vacuum. Crude product was purified by flash chromatography on silica. The pure product (colorless oil) was kept under argon at −18° C. prior its use. Phosphoroamidate L-5 was used as a 0.1M solution in anhydrous acetonitrile. Yield: 430 mg (58.3%); TLC: 16% Ethyl acetate, 4% Triethyl amine, 80% Hexane; Rf: 0.37. $^1$H and 31P-NMR-spectrum were in accordance with the proposed structure.

Evidence of Increased Bioavailability

We tested bioavailability of an examplary glinkoside, 5'-0 glucose-tritiated thymidine (D-G-L-Thy) by comparing incorporation of free thymidine with incorporation of D-G-L-Thy in a simple in vitro assay. In that assay we used Lung Cancer Cell line 177 cells (human Non-small Lung Carcinoma) growing in 10% Fetal Calf-Supplemented Medium (SSM) and in Serum-Free Medium (SFM). The cells were treated with free thymidine and with conjugated thymidine (D-G-L-Thy) for 4 and 24 hours. D-G-L-*Thy was synthesized using isotope dilution technique (1 part of Hot Thy:100 parts of Cold Thy). Stock solution was prepared having a mean value of cpm: Thy: 481,660 and 5'-0-conjugate: 467,242 (CORR. FACTOR: 1.03). The following results were obtained (mean values):

| Media | Thy | 5'-0-conjugate | 5'-0-conjugate/Thy |
|---|---|---|---|
| SSM (4 hr) | 2,945.0 | 4,089.4 | 1.39 |
| SFM (4 hr) | 1,119.6 | 2,022.4 | 1.39 |
| SSM (24 hr) | 12,395.7 | 16,063.9 | 1.34 |
| SFM (24 hr) | 5,869.8 | 8,230.7 | 1.44 |

In all conditions, incorporation of thymidine released from the D-G-L-Thy compound was improved over the control. These data indicate that thymidine can be released from the D-G-L-Thy complex in the cells due to the presence of phosphodiesterases, and that the released thymidine could thereafter be incorporated into DNA. It is rather unlikely that thymidine would have been released enzymatically from the complex extracellularly because such medium is phosphodiesterase-free.

Thus, our data demonstrates that the glinkoside compound D-G-L-Thy is taken up by cells as a prodrug, and is changed intracellularly to free thymidine and free glucose. Since the uptake together with parallel and subsequent (out- and in-cell) prodrug hydrolysis are kinetically complex, the experiment, at this stage, can be simply interpreted as follows:

The glinkoside uptake is very high, and most probably much higher than Thymidine uptake itself).

Intracellular hydrolysis of the prodrug is fast enough to liberate a sufficient quantity of free drug intracellularly.

This represents a good sign for a possible uptake of the glinkoside via the GLUT system.

Treatment Using Glinkosides

Glinkosides can be used to enhance the absorption, distribution and cellular uptake of both existing and yet-to-be developed pharmaceutical formulations. For example, glinkosides can be used for in vitro, in vivo, and ex vivo control and treatment of normal, senescent and pathological cell growth, induction/prevention of apoptosis, induction/inhibition of cell differentiation, control of cell metabolism and behavior, virus propagation and activity in infected cells and functioning of virus-infected cells, and for treatment of neuro-degenerative diseases.

The invention has particular relevance to transport of various monosaccharides and specifically to functioning of glucose transporters expressed in various tissues an cells. Glucose transporters are directly involved in transport of various monosaccharides into cells (glucose, mannose, galactose and others). Some of these glucose transporters are characteristic of certain tissues (for example) or cell type (for example) or biological functioning (for example GLUT-1 ion fast growing normal and cancer cells). The fact that different types of glucose transporters are differentially expressed in different cells offers a possibility of cell-specific uptake or delivery of bio-active compounds therapeutically conjugated with saccharide as described herein.

1. Glucose transporters in fast growing cells. Non-growing (quiescent) normal cells activated by growth factors enter cell cycle and finally divide. Growth factors cause the cascade of event observed on the gene, mRNA, protein expression, and cell structure organization level. For example, short-term (0.5–1 hr) increasing expression of GLUT-1 mRNA and protein has been observed in the cells activated by growth factors (Endocrinology, 1990, 127, 2025). Sodium vanadate which is known as a non-specific growth stimulant has been able to induce GLUT-1 expression in normal 3T3 fibroblasts and in addition, extend the half-life of GLUT-1 mRNA 2–3 times (Endocrinology, 1990, 126, 2778).

An autocrine mechanism of uncontrolled proliferation of cancer cells has been well established. Cancer cell grow rapidly and express a very high level of GLUT-1. In this way, cancer cells uptake much more glucose than normal cells and utilize it for glycolysis. It has also been proven that high level of functional GLUT-1 protein expression is required for cancer growth. Any inhibition of GLUT-1 functioning in cancer cells caused by binding of GLUT-1-specific antibodies or binding of suramin significantly limits glucose uptake and the growth rate of the treated cells. These data indicate the necessity of high glucose uptake for maintaining a high rate of proliferation of cancer cells, specifically mediated by growth factor-dependent GLUT). Thus, breast, prostate, lung, glioma and other cancer cells show significantly increased levels of GLUT.

2. Glucose transporters in blood-brain-barrier. In order to cross the blood-brain barrier (BBB), drugs must penetrate the luminal and basal membranes of endothelial cells. This is possible by taking advantage of receptor mediated uptake, such as, for example, in the case of the anti-Parkinson drug L-Dopa. Dopamine itself cannot penetrate the blood-brain barrier. However, its natural precursor L-Dopa is transported across the blood-brain barrier via an amino acid carrier system.

Antisense oligonucleotides are highly charged molecules and exhibit very little transport through the brain capillary walls. By incorporating oligonucleotides into glinkosides as described herein, the transport of these potentially valuable antisense drugs should be greatly facilitated by uptake via the glucose transporters of the endothelial cells which constitute the BBB.

The glucose transport from blood into the neuronal and glial cells of the brain is mediated by two specific transporters localized at the brain capillary endothelium which constitutes the BBB (M. W. Brightman 1977, "Morphology of Blood-brain Interfaces" *Exp. Eye Res.* 25, 1–25). These two glucose transporters were identified as two different members of the sodium independent glucose transporter supergene family. While the glucose transporter type 3 isoform (GLUT-3) is localized at the neuronal cell membrane (S. Nagamatsu et al, J. Biol. Chem. 267, 467–472), the glucose transporter type 1 isoform (GLUT-1) is localized at the BBB (R. J. Boado and W. M. Partridge, *Biochem. Biophys. Res. Commun.* 166, 174–179 (1990). A glinkoside should be able to penetrate the BBB due to the abundance of GLUT-1 transporter systems. This would greatly improve the potential applications of antisense-oligonucleotides for neurodegenerative diseases of the CNS, such as, for example, Parkinson's disease and Alzheimers disease. The drug might be administered orally or by IV injection, and then distributed via the blood circulation to the brain, or alternatively it could be injected into the carotid artery to improve the local delivery to the brain.

3. Other targets which are particularly suited for application of glinkosides because of the presence of specific glucose transporters include neural cells, liver, intestine, adipose tissue, muscles, and senescent cells.

Pharmaceutical Formulations Using Glinkosides

As with other pharmaceutical formulations, glinkosides may be adapted for administration to the body in a number of ways suitable for the selected method of administration, including orally, intravenously, intramuscularly, intraperitoneally, topically, and the like. In addition to comprising one or more different glinkosides, the subject pharmaceutical formulations may comprise one or more non-biologically active compounds, i.e., excipients, such as stabilizers (to promote long term storage), emulsifiers, binding agents, thickening agents, salts, preservatives, and the like.

Glinkosides can be employed in dosages and amounts which are conventional in the art for the underlying bio-active compound, but adjusted for more efficient absorption, transport and cellular uptake. Thus, for Ribavirin, which can be given orally at 1200 mg/day, the dosage of the corresponding glinkoside would include approximately 600 mg/day of Ribavirin, or less. The dosages may be administered all at once, or may be divided into a number of smaller doses which are then administered at varying intervals of time.

The dosage regimen may be adapted to provide the optimum therapeutic response. For example, the most preferred dosage will vary with the particular agent chosen, and during the course of administration the dose may be proportionally increased or reduced as indicated by the exigencies of the therapeutic situation.

Glinkosides may be administered in any convenient manner, such as by oral, intravenous, intraperitoneal, intramuscular, or subcutaneous or other known routes. For oral administration, glinkosides may be administered with an inert diluent or with an assimilable edible carrier, or glinkosides may be incorporated directly with the food of the diet. Orally administered glinkosides may be incorporated with excipients and used in the form of ingestible tablets, buccal tablets, troches, capsules, elixirs, suspension syrups, wafers, and the like.

The tablets, troches, pills, capsules and the like may also contain the following: a binder, such as gum tragacanth, acacia, cornstarch, or gelatin; excipients, such as dicalcium phosphate; a disintegrating agent such as corn starch, potato starch, alginic acid and the like; a lubricant such as magnesium stearate; and a sweetening agents, such as sucrose, lactose or saccharin; a flavoring agent such as peppermint, oil of wintergreen, or cherry flavoring. When the dosage unit is a capsule, it may contain, in addition to materials of the above type, a liquid carrier. Various other materials may also be present as coatings or to otherwise modify the physical form of the dosage unit. For instance, tablets, pills, or capsules may be coated with shellac, sugar or both. A syrup or elixir may contain sucrose as a sweetening agent, methyl and propylparabens as preservatives, a dye and flavoring such as cherry or orange flavor. Such additional materials should be substantially non-toxic in the amounts employed. Furthermore, the glinkosides may be incorporated into sustained-release preparations and formulations.

Formulations for parenteral administration may include sterile aqueous solutions or dispersions, and sterile powders for the extemporaneous preparation of sterile, injectable solutions or dispersions. The solutions or dispersions may also contain buffers, diluents, and other suitable additives, and may be designed to promote the cellular uptake of the glinkosides in the composition, e.g., the glinkosides may be encapsulated in suitable liposomes. Preferably the solutions and dispersions for parenteral administration are sterile and sufficiently fluid for proper administration, sufficiently stable for manufacture and use, and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by maintenance of the required particle size in the case of dispersion and by the use of surfactants.

Sterile injectable solutions are prepared by incorporating the active compounds in the required amount in the appropriate solvent with one or more of the various other ingredients described above, followed by sterilization. Dispersions may generally be prepared by incorporating the various sterilized active ingredients into a sterile vehicle which contains the basic dispersion medium and the required other ingredients from those listed above. In the case of sterile powders used to prepare sterile injectable solutions, the preferred methods of preparation are vacuum-drying and freeze-drying techniques which yield a powder of the active ingredient plus any additional desired ingredient from previously sterile-filtered solutions.

Pharmaceutical formulations for topical administration may be especially useful with certain bio-active compounds for localized treatment. Formulations for topical treatment included ointments, sprays, gels, suspensions, lotions, creams, and the like. Formulations for topical administration may include, in addition to the subject glinkosides, known carrier materials such as isopropanol, glycerol, paraffin, stearyl alcohol, polyethylene glycol, etc. The pharmaceutically acceptable carrier may also include a known chemical absorption promoter. Examples of absorption promoters are e.g., dimethylacetamide U.S. Pat. No. 3,472,931), trichloroethanol or trifluoroethanol (U.S. Pat. No. 3,891,757), certain alcohols and mixtures thereof (British Patent No. 1,001, 949), and British patent specification No. 1,464,975.

Solutions of the glinkosides may be stored and/or administered as free base or pharmacologically acceptable salts, and may advantageously be prepared in water suitably mixed with a surfactant such as hydroxypropylcellulose. Dispersions can also be prepared in glycerol, liquid polyethylene glycols, and mixtures thereof and in oils. These compositions and preparations may advantageously contain a preservative to prevent the growth of microorganisms.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents such as sodium chloride. Prolonged delivery of injectable compositions can be brought about by the use of agents which delay absorption, such as aluminum monostearate and gelatin.

The compositions and preparations described preferably contain at least 0.1% of active glinkoside. The percentage of the compositions and preparations may, of course, be varied, and may contain between about 2% and 60% of the weight of the amount administered. The amount of active compounds in such therapeutically useful compositions and preparations is such that a suitable dosage will be obtained.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the therapeutic active ingredients, its use in the therapeutic compositions and preparations is contemplated. Supplementary active ingredients can also be incorporated into the compositions and preparations.

In addition to the therapeutic uses of the subject glinkosides, the glinkosides may also be used as a laboratory tool for the study of absorption, distribution, cellular uptake, and efficacy.

Equivalents

The foregoing written specification is considered to be sufficient to enable one skilled in the art to practice the invention. Indeed, various modifications of the above-described makes for carrying out the invention which are obvious to those skilled in the field of organic chemistry or related fields are intended to be within the scope of the following claims.

What is claimed is:

1. A compound having the general form MS-LINK-BAM, where MS is a monosaccharide, LINK is a linker, BAM is a bioactive material, MS is covalently bound to LINK at a position other than the MS $C_1$ carbon, and LINK is covalently linked to BAM, where the compound is more bioactive than BAM alone.

2. The compound of claim 1 wherein MS comprises a hexose.

3. The compound of claim 2 wherein the hexose is glucose.

4. The compound of claim 1 wherein MS comprises a ribose.

5. The compound of claim 1 wherein MS comprises a pentose.

6. The compound of claim 1 wherein LINK comprises a straight chain alkane having between 4 and 16 carbons, inclusive.

7. The compound of claim 1 wherein BAM comprises Ribavirin.

8. The compound of claim 1 wherein the MS-LINK bond is differentially cleavable from the LINK-BAM bond.

9. The compound of claim 8 wherein the MS-LINK bond is stronger than the LINK-BAM bond under physiological conditions.

10. A method of synthesizing a glinkoside comprising the following steps:

provinding a monosaccharide, a linker having an $\alpha$ and an $\omega$ position, and a bioactive material;

protecting a functionality at the $\omega$ position of the linker;

forming a non-glycosidic chemical bond between the monosaccharide and the $\alpha$ position of the linker;

deprotecting the functionality at the $\omega$ position of the linker;

forming a chemical bond between the $\omega$ position of the linker and the bioactive material.

11. A method of increasing the bioavailability of a bioactive material by covalently bonding the bioactive material to a linker, and covalently bonding the linker to a sugar at one of the sugar's $C_2$, $C_3$, $C_4$ and $C_6$ carbons.

12. A method of treating a disease in a patient comprising the steps of:

providing a glinkoside in a pharmaceutically acceptable form;

administering an effective amount of the glinkoside to the patient.

13. A compound having the general form MS-LINK-BAM, where MS is a monosaccharide, LINK is a linker, BAM is a bioactive material, MS is covalently bound to LINK at a position other than the MS $C_1$ carbon, and LINK is covalently linked to BAM, where the compound is more actively transported across a target cell membrane than BAM alone.

14. The compund of claim 13 wherein BAM is readily cleavable by the target cell.

15. The compund of claim 13 wherein BAM is not readily cleavable by the target cell.

* * * * *